US008080661B2

(12) United States Patent
Wang et al.

(10) Patent No.: US 8,080,661 B2
(45) Date of Patent: Dec. 20, 2011

(54) PROCESSES FOR THE SYNTHESIS OF TERTIARY AMINES

(75) Inventors: Peter X. Wang, Clarkson Valley, MO (US); Tao Jiang, St. Louis, MO (US); David W. Berberich, St. Peters, MO (US)

(73) Assignee: Mallinckrodt LLC, Hazelwood, MO (US)

( * ) Notice: Subject to any disclaimer, the term of this patent is extended or adjusted under 35 U.S.C. 154(b) by 329 days.

(21) Appl. No.: 12/586,843

(22) Filed: Sep. 29, 2009

(65) Prior Publication Data

US 2010/0081819 A1 Apr. 1, 2010

Related U.S. Application Data

(60) Provisional application No. 61/194,698, filed on Sep. 30, 2008.

(51) Int. Cl.
*C07D 221/28* (2006.01)
(52) U.S. Cl. ........................................... 546/74
(58) Field of Classification Search .................... 546/74
See application file for complete search history.

(56) References Cited

U.S. PATENT DOCUMENTS

| 4,141,897 | A | 2/1979 | Olofson et al. |
| 4,176,186 | A | 11/1979 | Goldberg et al. |
| 5,668,285 | A | 9/1997 | Rice et al. |
| 2008/0214817 | A1 | 9/2008 | Dlubala |

FOREIGN PATENT DOCUMENTS

| EP | 0 039 066 | 11/1981 |
| GB | 2 438 399 | 11/2007 |
| GB | 2 438 401 | 11/2007 |
| WO | WO 2007/137785 | 12/2007 |

OTHER PUBLICATIONS

Chi et al., "Synthesis of Naltrexone", Shanghai Diyi Yixueyuan Xuebao, 1984, 11(6), pp. 474-475.
Greiner et al., "Synthesis and Biological Evaluation of 14-Alkoxymorphinans. 18. N-Substituted 14-phenylpropyloxymorphinan-6-ones with Unanticipated Agonist Properties: Extending the Scope of common Structure-Activity Relationships", Journal of Medicinal Chemistry, 2003, 46(9), pp. 1758-1763.
Hasegawa et al., "Affinity Identification of -opioid Receptors Using Latex Nanoparticles", Bioorganic & Medicinal Chemistry Letters, 2006, 16(1), pp. 158-161.
Lattanzi et al., "Synthesis and Biological Evaluation of 14-Alkoxymorphinans.22.Influence of the 14-Alkoxy Group and the Substitution in Position 5 in 14-Alkoxymorphinan-6-ones on in Vitro and in Vivo Activities", Journal of Medicinal chemistry, 2005, 48(9), pp. 3372-3378.
Olofson et al., "A New Reagent for the Selective, High-Yield N-Dealkylation of Tertiary Amines: Improved Syntheses of Naltrexone and Nalbuphine", Journal of Organic Chemistry, 1984, 49(11), pp. 2081-2082.
Rogers et al., "Synthesis, In Vitro Acetylcholine-Storage-Blocking Activities, and Biological Properties of Derivatives and Analogs of Trans-2-(4-Phenylpiperidino)Cyclohexanol (Vesamicol)", Journal of Medicinal Chemistry, 1989, 32(6), pp. 1217-1230.
Schmidhammer et al., "Synthesis and biological Evaluation of 14-Alkoxymorphinans. Part 4. Opioid Agonists and Partial Opioid Agonists in a Series of N-(cyclobutylmethyl)-14-Methoxymorphinan-6-Ones", Helvetica chimica Acta, 1989, 72(6), pp. 1233-1240.
Ullrich et al., "Derivatives of 17-(2-methylallyl)-substituted Noroxymorphone: Variation of the Delta Address and Its Effects on Affinity and Selectivity for the Delta Opioid Receptor", Bioorganic & Medicinal Chemistry Letters, 2001, 11(21), pp. 2883-2885.
Park et al., "A highly selective kapp-opioid receptor agonist with low addictive potential and dependence liability", Bioorganic & Medicinal Chemistry Letters, 16(13), 2006, pp. 3609-3613, XP 002561404 & Park et al., "Supporting Information. A highly selective kapp-opioid receptor agonist with low addictive potential and dependence liability", Bioorganic & Medicinal Chemistry Letter, 16(13), 2006, pp. S1-S11, XP 002565760.
Kobylecki et al., "Common Anionic Receptor Site Hypothesis: Its Relevance to the antagonist Action of Naloxone", J. Med. Chem., 25, 1982, pp. 116-120, XP 002561405.
Archer et al., "Hybromet: A Ligand for Purifying Opiod Receptors", J. Med. Chem., 28, 1985, pp. 1950-1953, XP 002558539.
Ullrich et al., "Derivatives of 17-(2-methylallyl)-substituted Noroxymorphone: Variation of the Delta Address and Its Effects on Affinity and Selectivity for the Delta Opioid Receptor", Bioorganic & Medicinal Chemistry Letters II, 2001, pp. 2883-2885.
Uff et al., "NMR Spectra and Stereochemistry of some 7-Substituted 6,14-Bridged Thebaine Derivatives", Magnetic Resonance in Chemistry, 23(6), 1985, pp. 454-458, XP 002558538.

*Primary Examiner* — Taofiq A Solola

(57) ABSTRACT

The invention provides processes for the preparation of morphinans having a tertiary amine. In particular, the present invention provides processes for the formation of tertiary amine alkaloids by direct N-alkylation of secondary amine alkaloids, the processes co-mediated by an alkylating agent and a protic solvent or a mixture of a protic solvent and an aprotic solvent.

22 Claims, No Drawings

PROCESSES FOR THE SYNTHESIS OF TERTIARY AMINES

CROSS REFERENCE TO RELATED APPLICATIONS

This application claims priority from U.S. Provisional Application No. 61/194,698, filed on Sep. 30, 2008, which is hereby incorporated by reference in its entirety.

FIELD OF THE INVENTION

The present invention generally relates to processes for the synthesis of tertiary amines. In particular, the present invention provides processes for the formation of morphinan compounds containing a tertiary amine.

BACKGROUND OF THE INVENTION

"Nal" opiates are a class of alkaloids containing tertiary amines which includes naltrexone, naloxone, nalbuphone, (+)-naltrexone, (+)-naloxone, (+)-nalbuphone, α- or β-naltrexol, α- or β-naloxol, and α- or β-nalbuphine. These opiates share a basic morphinan chemical structure and include a tertiary amine at position C-17. They are particularly useful as competitive antagonists of opioid compounds, and as such are widely used in treating substance abuse and addiction.

Tertiary amines can be synthesized via direct alkylation of secondary amines. For example, naltrexone can be synthesized via direct alkylation of noroxymorphone using cyclopropylmethylbromide as an alkylating agent. From a theoretical standpoint, the direct alkylation of secondary amines with alkyl halides is the most straight-forward method for the synthesis of tertiary amines. However, noroxymorphone is relatively costly and direct N-alkylation typically results in relatively poor yields of only about 60%-80%. Moreover, the direct route produces unacceptably high levels of undesired side products via the simultaneous but unwanted N-alkylation of tertiary amines, and also O-alkylation of the phenol group at position C-3. To reduce cost and improve yield, other synthetic routes have been sought and investigated. Indirect alkylation methods have been described, such as those involving metal-mediated N-alkylation or reductive amination of secondary amines. However, indirect methods are remain limited by relatively modest yields, and are further limited by the difficulty in completely removing the required toxic metal reagents, and by poor commercial availability of the required alkylation reagents (e.g., cyclopropylmethylaldhyde). Accordingly, a need exists for improved synthetic methods for producing morphinan compounds containing a tertiary amine.

SUMMARY OF THE INVENTION

The invention provides a process for the preparation of a morphinan having a tertiary amine by direct N-alkylation of a morphinan having a secondary amine. The process is co-mediated by an alkylating agent and a protic solvent or a mixture of a protic solvent and an aprotic solvent. The process provides a synthetic route that highly favors N-alkylation of secondary amines over the formation of unwanted side products otherwise produced in quantity by direct N-alklylation. This novel synthetic route may be utilized to produce a variety of compounds including biologically active alkaloids containing tertiary amines such as certain opioids and opioid antagonists.

Briefly, therefore, in one aspect the present invention encompasses a process for the preparation of a morphinan comprising a tertiary amine. The process comprises contacting a morphinan comprising a secondary amine with a protic solvent, and an alkylating agent. The alkylating agent is selected from the group consisting of alkyl halides comprising $R^{17}X$, and dialkyl sulfate comprising $R^{17}_2SO4$, wherein $R^{17}$ is selected from the group consisting of hydrocarbyl and substituted hydrocarbyl, and X is selected from the group consisting of chloride, bromide, and iodide. The process results in the formation of the morphinan comprising a tertiary amine comprising $R^{17}$.

In another aspect the present invention encompasses a process for the preparation of a compound comprising Formula (II) from a compound comprising Formula (I) according to

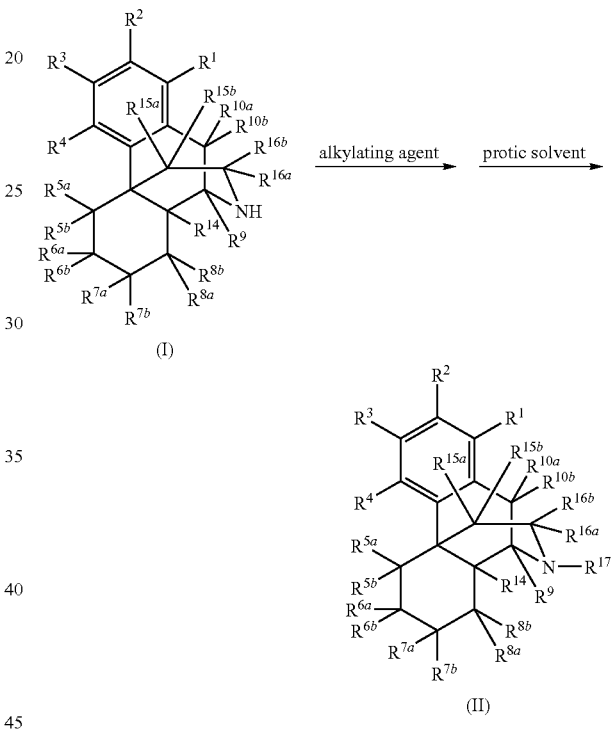

the following reaction:

The alkylating agent is selected from the group consisting of alkyl halide represented by the formula $R^{17}X$, and dialkyl sulfate represented by the formula $R^{17}_2SO4$, wherein $R^{17}$ is selected from the group consisting of hydrocarbyl and substituted hydrocarbyl, and X is selected from the group consisting of Cl, Br and I. For each of the compounds comprising Formula (I) or Formula (II) the variables stand for the following:

$R^1$, $R^2$, $R^3$, and $R^4$ are independently selected from the group consisting of hydrogen, halogen, hydroxyl, SH, $-SR^{1611}$, $-OR^{1611}$, and $-NR^{1611}R^{1612}$; hydrocarbyl, and substituted hydrocarbyl; $R^{5a}$, $R^{5b}$, $R^{6a}$, $R^{6b}$, $R^{7a}$, $R^{7b}$, $R^{8a}$, $R^{8b}$, $R^9$, $R^{10a}$, $R^{10b}$, $R^{15a}$, $R^{15b}$, $R^{16a}$ $R^{16b}$, and $R^{14}$ are independently selected from the group consisting of hydrogen, halogen, hydroxyl, SH, $-SR^{1611}$, $-OR^{1611}$, and $-NR^{1611}R^{1613-}$, hydrocarbyl, and substituted hydrocarbyl, wherein any pair of $R^{\#a}$ and $R^{\#b}$ wherein # is any one of 5, 6, 7, 8, 9, 10, 15, 16, optionally together form a group selected from the group consisting of =O, =S, and =$NR^{1613}$;

$R^{1611}$, $R^{1612}$ and $R^{1613}$ are independently selected from the group consisting of hydrocarbyl, and substituted hydrocarbyl;

provided that one or more of $R^1$, $R^2$, $R^3$, $R^4$, $R^{5a}$, $R^{5b}$, $R^{6a}$, $R^{6b}$, $R^{7a}$, $R^{7b}$, $R^{8a}$ $R^{8b}$, $R^{9a}$, $R^{10a}$ $R^{10b}$, $R^{15a}$ $R^{15b}$, $R^{16a}$ $R^{16b}$, and $R^{14}$ may come together to form one or more carbocyclic or heterocyclic rings.

In yet another aspect the present invention encompasses a process for the preparation of a compound comprising Formula (IIa) from a compound comprising Formula (Ia) according to the following reaction:

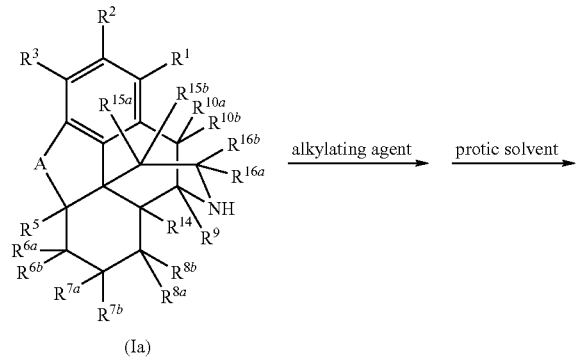

(Ia)

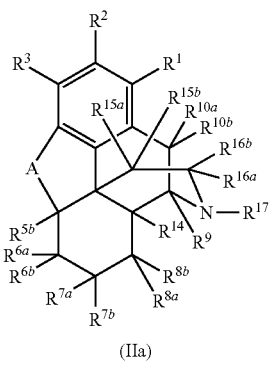

(IIa)

The alkylating agent is selected from the group consisting of alkyl halide represented by the formula $R^{17}X$, and dialkyl sulfate represented by the formula $R^{17}{}_2SO_4$, wherein $R^{17}$ is selected from the group consisting of hydrocarbyl and substituted hydrocarbyl, and X is selected from the group consisting of Cl, Br and I. For each of the compounds comprising Formula (Ia) or Formula (IIa) the variables stand for the following:

A is a heteroatom selected from oxygen and sulfur;

$R^1$, $R^2$, $R^3$, and $R^4$ are independently selected from the group consisting of hydrogen, halogen, hydroxyl, SH, —$SR^{1611}$, —$OR^{1611}$, and —$NR^{1611}R^{1612}$; hydrocarbyl, and substituted hydrocarbyl;

$R^5$, $R^{6a}$, $R^{6b}$, $R^{7a}$, $R^{7b}$, $R^{8a}$ $R^{8b}$, $R^9$, $R^{10a}$ $R^{10b}$, $R^{15a}$ $R^{15b}$, $R^{16a}$ $R^{16b}$, and $R^{14}$ are independently selected from the group consisting of hydrogen, halogen, hydroxyl, SH, —$SR^{1611}$, —$OR^{1611}$, and —$NR^{1611}R^{1613}$; hydrocarbyl, and substituted hydrocarbyl, wherein any pair of $R^{\#a}$ and $R^{\#b}$ wherein # is any one of 6, 7, 8, 9, 10, 15, 16, optionally together form a group selected from the group consisting of =O, =S, and =$NR^{1613}$;

$R^{1611}$, $R^{1612}$ and $R^{1613}$ are independently selected from the group consisting of hydrocarbyl, and substituted hydrocarbyl;

provided that one or more of $R^1$, $R^2$, $R^3$, $R^4$, $R^5$, $R^{6a}$, $R^{6b}$, $R^{7a}$, $R^{7b}$, $R^{8a}$ $R^{8b}$, $R^{9a}$, $R^{10a}$ $R^{10b}$, $R^{15a}$ $R^{15b}$, $R^{16a}$ $R^{16b}$, and $R^{14}$ may come together to form one or more carbocyclic or heterocyclic rings.

Other features and iterations are described in more detail below.

DETAILED DESCRIPTION OF THE INVENTION

The invention provides an efficient synthetic route for the production of a morphinan compound having a tertiary amine utilizing a direct N-alkylation process starting with a morphinan compound having a secondary amine. The process is co-mediated by an alkylating agent and a protic solvent. It has been discovered that co-mediation of the alkylation reaction by a protic solvent preferentially drives the formation of the desired tertiary amine over the formation of side products resulting from the alkylation of tertiary amine products and the O-alkylation of the phenol group at position C-3. Without being bound by theory, it is believed that the addition of a protic solvent such as water, alcohol or acid increases the reactivity difference between the secondary amine and other species with respect to the alkylating agent. The intended N-alkylation of secondary amines occurs much faster than the unwanted N-alkylation of newly formed tertiary amines thus forming quaternary ammonium salts, and than the O-alkylation of the phenol group at position C-3. The result is a more efficient process that provides yields representing a substantial increase over the typical yield of 60% to 80% using direct alkylation. In addition the process avoids the need for heavy metal or other toxic reagents that are difficult to remove, and the process is highly scalable. The method is equally applicable to the production of both naturally-occurring and synthetic opiates, such as for example the pharmaceutically significant "nal" opiates, and can be used equally well to prepare (+) and (−) enantiomers. It has also been discovered that addition of a proton acceptor to the reaction mixture further favors the desired reaction by further limiting the reactivity of tertiary amines and phenol groups, thereby providing yields of at Least about 90%, about 95%, about 98% or about 99% as set forth in the Examples.

(I) Synthesis of Compounds Comprising Formula (II)

In one aspect the process of the invention comprises a direct N-alkylation of a morphinan compound comprising a secondary amine to produce a morphinan compound comprising a tertiary amine, using an alkylating agent in the presence of a protic solvent. In an exemplary embodiment the process comprises an N-alkylation of a morphinan compound having a secondary amine at position C-17, namely a compound comprising Formula (I), using an alkylating agent in the presence of a protic solvent to produce a morphinan compound having a tertiary amine at position C-17 comprising Formula (II). For purposes of illustration, Reaction Scheme 1 depicts production of compound comprising Formula (II) in accordance with one aspect of the invention:

Reaction Scheme 1

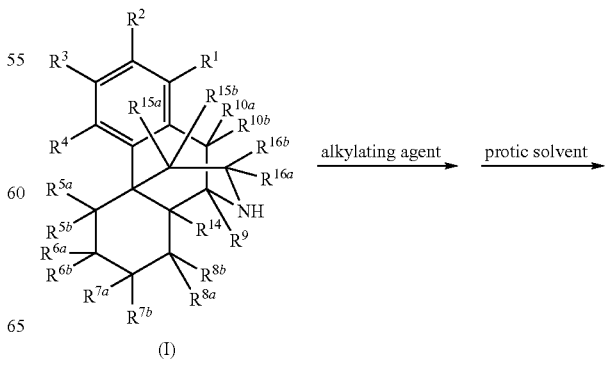

(I)

-continued

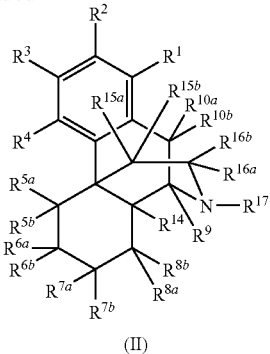

(II)

wherein:
the alkylating agent is selected from the group consisting of alkyl halide represented by the formula $R^{17}X$, and dialkyl sulfate represented by the formula $R^{17}{}_2SO_4$, wherein $R^{17}$ is selected from the group consisting of hydrocarbyl and substituted hydrocarbyl, and X is selected from the group consisting of Cl, Br and I;

$R^1$, $R^2$, $R^3$, $R^4$ are independently selected from the group consisting of hydrogen, halogen, hydroxyl, SH, $-SR^{1611}$, $-OR^{1611}$, and $-NR^{1611}R^{1612}$; hydrocarbyl, and substituted hydrocarbyl;

$R^1$, $R^2$, $R^3$, $R^4$, $R^{5a}$, $R^{5b}$, $R^{6a}$, $R^{6b}$, $R^{7a}$, $R^{7b}$ $R^{8a}$, $R^{8b}$, $R^9$, $R^{10a}$, $R^{10b}$, $R^{15a}$, $R^{15b}$, $R^{16a}$, $R^{16b}$, and $R^{14}$ are independently selected from the group consisting of hydrogen, halogen, hydroxyl, SH, $-SR^{1611}$, $-OR^{1611}$, and $-NR^{1611}R^{1613}$; hydrocarbyl, and substituted hydrocarbyl, wherein any pair of R#a and R#b wherein # is any one of 5, 6, 7, 8, 9, 10, 15, 16, optionally together form a group selected from the group consisting of =O, =S, and =NR$^{1613}$;

$R^{1611}$, $R^{1612}$ and $R^{1613}$ are independently selected from the group consisting of hydrocarbyl, and substituted hydrocarbyl;

provided that one or more of $R^1$, $R^2$, $R^3$, $R^4$, $R^{5a}$, $R^{5b}$, $R^{6a}$, $R^{6b}$, $R^{7a}$, $R^{7b}$ $R^{8a}$, $R^{8b}$, $R^9$, $R^{10a}$, $R^{10b}$, $R^{11}$, $R^{12}$, $R^{13}$, $R^{14}$, $R^{15a}$, $R^{15b}$, $R^{16a}$, $R^{16b}$, and $R^{14}$ may come together to form one or more carbocyclic or heterocyclic rings.

In one embodiment, the compound comprising Formula (II) is a compound comprising Formula (IIa) in which $R^4$ and $R^{5a}$ come together to form a heterocyclic ring in which A is a heteroatom selected from oxygen and sulfur:

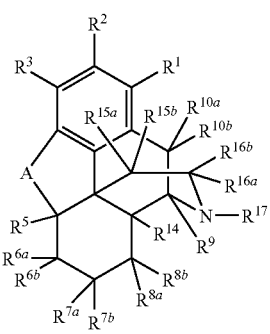

(IIa)

wherein $R^1$, $R^2$, $R^3$, and $R^4$ are as described for compounds of Formula II;

$R^5$, $R^{6a}$, $R^{6b}$, $R^{7a}$, $R^{7b}$, $R^{8a}$ $R^{8b}$, $R^9$, $R^{10a}$ $R^{10b}$, $R^{15a}$ $R^{15b}$, $R^{16a}$ $R^{16b}$, and $R^{14}$ are independently selected from the group consisting of hydrogen, halogen, hydroxyl, SH, $-SR^{1611}$, $-OR^{1611}$, and $-NR^{1611}R^{1613}$; hydrocarbyl, and substituted hydrocarbyl, wherein any pair of R#a and R#b wherein # is any one of 6, 7, 8, 9, 10, 15, 16, optionally together form a group selected from the group consisting of =O, =S, and =NR$^{1613}$, $R^{1611}$, $R^{1612}$ and $R^{1613}$ are independently selected from the group consisting of hydrocarbyl, and substituted hydrocarbyl;

provided that one or more of $R^1$, $R^2$, $R^3$, $R^4$, $R^5$, $R^{6a}$, $R^{6b}$, $R^{7a}$, $R^{7b}$, $R^{8a}$ $R^{8b}$, $R^{9a}$, $R^{10a}$ $R^{10b}$, $R^{15a}$ $R^{15b}$, $R^{16a}$ $R^{16b}$, and $R^{14}$ may come together to form one or more carbocyclic or heterocyclic rings, and wherein the alkylating agent is as described for Reaction Scheme 1.

For purposes of illustration, Reaction Scheme 2 depicts production of a compound comprising Formula (IIa) from a compound of Formula I comprising a compound of Formula (Ia) in accordance with another aspect of the invention:

Reaction Scheme 2

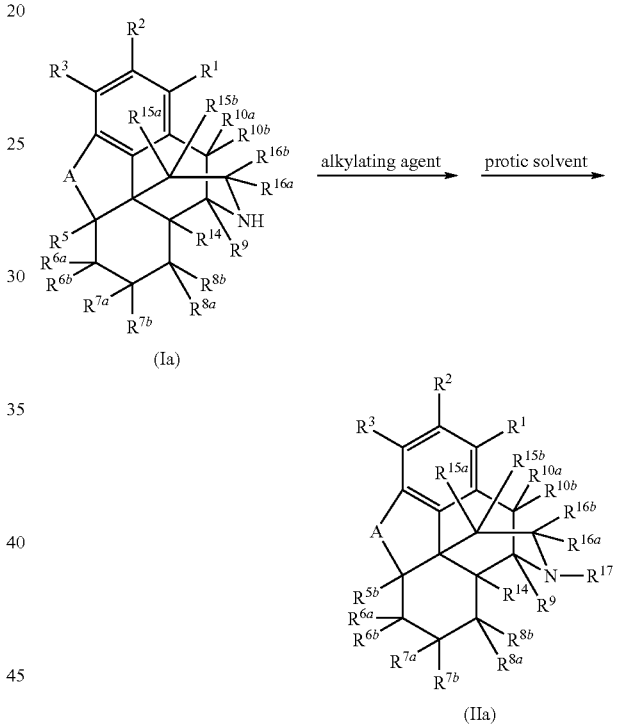

wherein A is a heteroatom selected from oxygen and sulfur,
wherein the alkylating agent and $R^{17}$ are as described for Reaction Scheme 1,
wherein $R^1$, $R^2$, $R^3$, $R^4$ are as described for Reaction Scheme 1,
wherein $R^5$, $R^{6a}$, $R^{6b}$, $R^{7a}$, $R^{7b}$, $R^{8a}$ $R^{8b}$, $R^9$, $R^{10a}$ $R^{10b}$, $R^{15a}$ $R^{15b}$, $R^{16a}$ $R^{16b}$, and $R^{14}$ are independently selected from the group consisting of hydrogen, halogen, hydroxyl, SH, $-SR^{1611}$, $-OR^{1611}$, and $-NR^{1611}R^{1613}$; hydrocarbyl, and substituted hydrocarbyl, wherein any pair of R#a and R#b wherein # is any one of 6, 7, 8, 9, 10, 15, 16, optionally together form a group selected from the group consisting of =O, =S, and =NR$^{1613}$, $R^{1611}$, $R^{1612}$ and $R^{1613}$ are independently selected from the group consisting of hydrocarbyl, and substituted hydrocarbyl;

provided that one or more of $R^1$, $R^2$, $R^3$, $R^4$, $R^5$, $R^{6a}$, $R^{6b}$, $R^{7a}$, $R^{7b}$, $R^{8a}$ $R^{8b}$, $R^{9a}$, $R^{10a}$ $R^{10b}$, $R^{15a}$ $R^{15b}$, $R^{16a}$ $R^{16b}$, and $R^{14}$ may come together to form one or more carbocyclic or heterocyclic rings.

In an exemplary embodiment of the process, the compound having Formula (I) is a compound comprising Formula (Ia-1) wherein A is oxygen. For purposes of illustration, Reaction Scheme 3 depicts production of a compound comprising Formula (IIa-2) from a compound of Formula I comprising a compound of Formula (Ia-1) in accordance with another aspect of the invention:

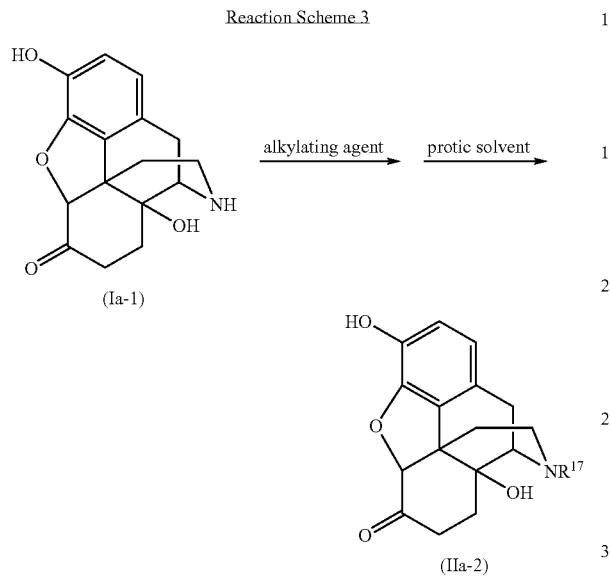

wherein the alkylating agent and $R^{17}$ are as described for Reaction Scheme 1.

In another exemplary embodiment, the compound of Formula (I) is a compound comprising Formula (Ib-1), the alkylating agent is cyclopropylmethylbromide and the process produces a compound comprising Formula (IIb-2) according to Reaction Scheme 4:

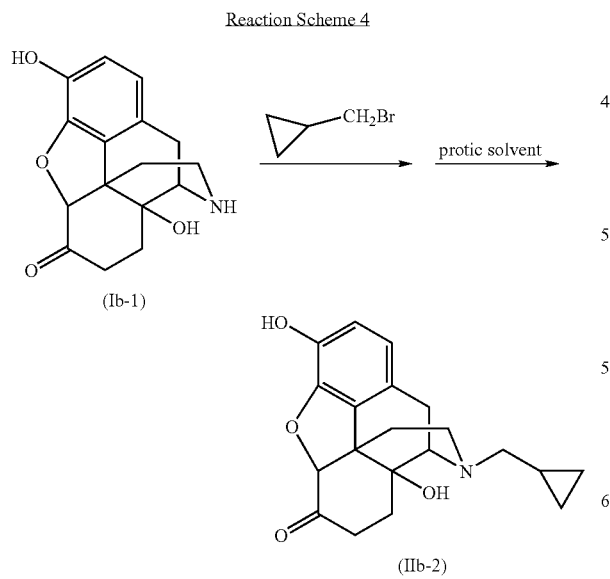

In another exemplary embodiment, the compound of Formula (I) is a compound comprising Formula (Ic-1), wherein the alkylating agent is as described for Reaction Scheme 1 for producing compounds of Formula (II) and the process produces a compound comprising Formula (IIc-2) according to Reaction Scheme 5:

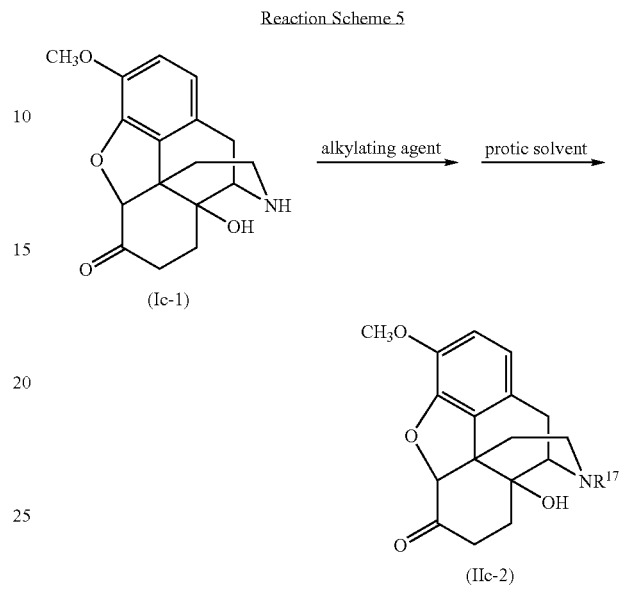

In another exemplary embodiment, the compound of Formula (I) is a compound comprising Formula (Id-1), wherein the alkylating agent is cyclopropylmethylbromide and the process produces a compound comprising Formula (IId-2) according to Reaction Scheme 6:

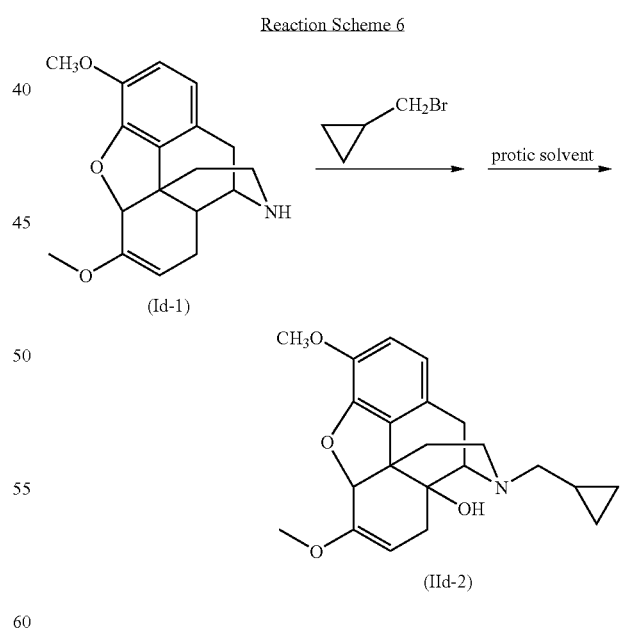

(a) Reaction Mixture

The process commences with formation of a reaction mixture by combining a compound comprising Formula (I), with an alkylating agent in the presence of a protic solvent. A variety of compounds having Formula (I) are suitable for use in the process. In one embodiment of the process, the

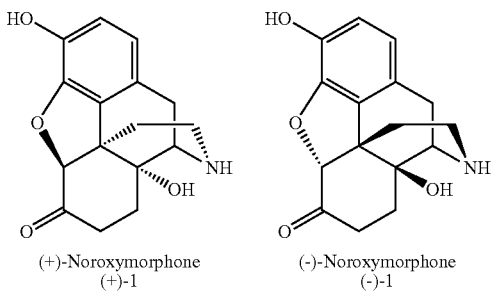

(+)-Noroxymorphone (+)-1      (-)-Noroxymorphone (-)-1 compound comprising Formula (I) is either the (+) or (-) enantiomer of noroxymorphone:

As further detailed in the Examples, using cyclopropylmethylbromide as the alkylating agent and noroxymorphone as the compound comprising Formula (I), the process is used to prepare the (+) or (-) enantiomer of naltrexone as the compound comprising Formula (II):

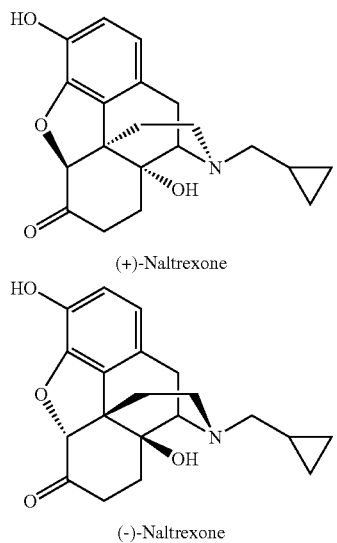

(+)-Naltrexone (-)-Naltrexone

In another embodiment, noroxymorphone or a derivative thereof is the compound comprising Formula (I) according to the process, using an alkyl halide as the alkylating agent, to prepare the (+) or (-) enantiomer of N—R-noroxymorphone as the compound comprising Formula (II), wherein R is selected from the group consisting of hydrocarbyl and substituted hydrocarbyl:

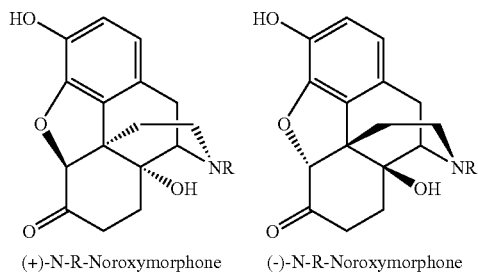

(+)-N-R-Noroxymorphone      (-)-N-R-Noroxymorphone

In another embodiment of the process, the compound having Formula (I) is either the (+) or (-) enantiomer of noroxycodone:

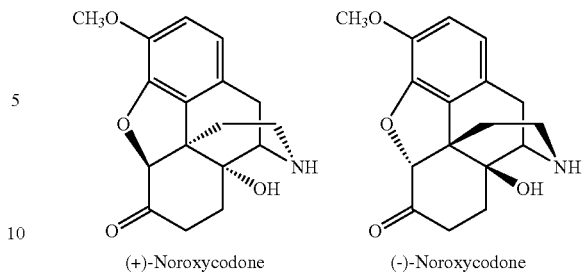

(+)-Noroxycodone      (-)-Noroxycodone

Noroxycodone is used as the compound comprising Formula (I) according to the process, using an alkyl halide as the alkylating agent, to prepare the (+) or (-) enantiomer of N—R-noroxycodone as the compound comprising Formula (II):

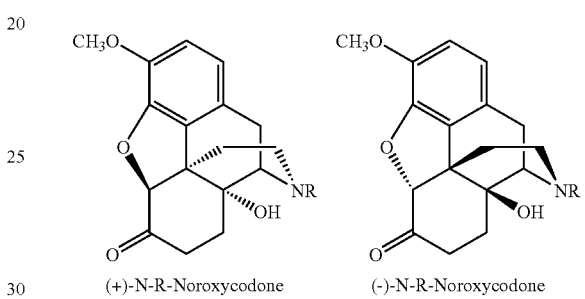

(+)-N-R-Noroxycodone      (-)-N-R-Noroxycodone

In another embodiment of the process, the compound having Formula (I) is either the (+) or (-) enantiomer of 6,7-dihydro-northebaine:

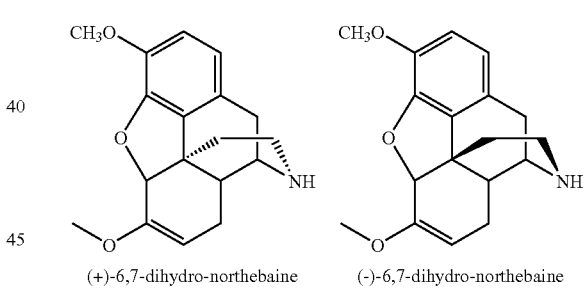

(+)-6,7-dihydro-northebaine      (-)-6,7-dihydro-northebaine

As described in Example 4, 6,7-dihydro-northebaine is used as the compound comprising Formula (I) according to the process, using cyclopropylmethylbromide as the alkylating agent, to prepare the (+) or (-) enantiomer of N-cyclopropylmethyl-6,7-dihydro-northebaine as the compound comprising Formula (II):

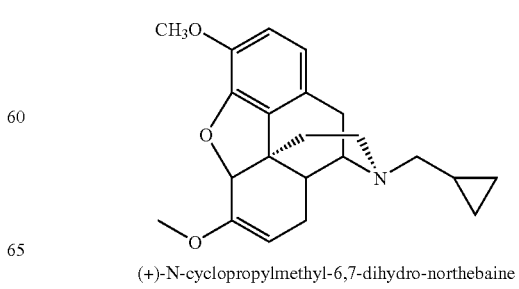

(+)-N-cyclopropylmethyl-6,7-dihydro-northebaine

-continued

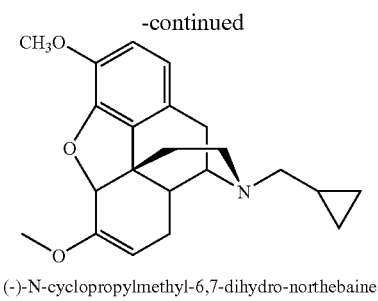

(−)-N-cyclopropylmethyl-6,7-dihydro-northebaine

Other compounds comprising Formula (II) that can be prepared according to the process include the (+) and (−) enantiomers of naloxone and nalbuphone:

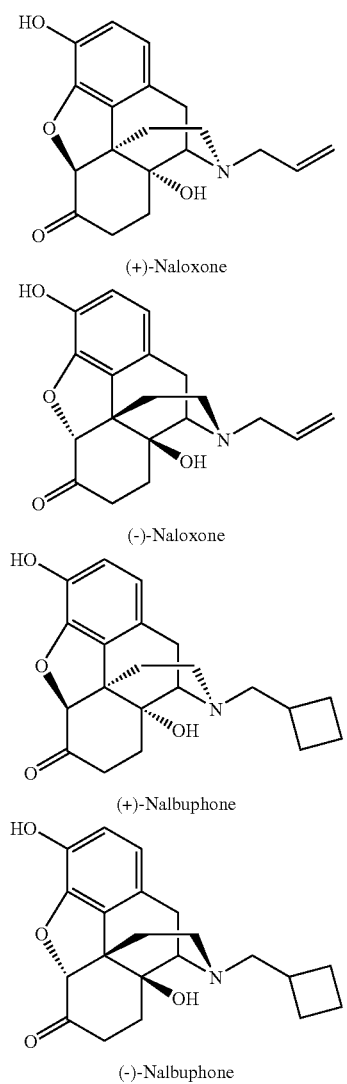

(+)-Naloxone (−)-Naloxone (+)-Nalbuphone (−)-Nalbuphone

The reaction mixture includes the alkylating agent. Generally the alkylating agent is an alkyl halide represented by the formula $R^{17}X$, or a dialkyl sulfate represented by the formula $R^{17}{}_2SO_4$, wherein $R^{17}$ is selected from the group consisting of hydrocarbyl and substituted hydrocarbyl, and X is selected from the group consisting of Cl, Br and I. In one embodiment, the alkylating agent is an alkyl halide having from one to ten carbon atoms, or a substituted alkyl halide having from one to ten carbon atoms. Non-limiting examples of suitable alkyl halides are halidemethylcyclopropane, halidemethylbutane, and halide{−}$CH_2CHCH_2$. In an exemplary embodiment the alkylating agent is cyclopropylmethylbromide. The amount of alkylating agent in the reaction mixture may vary but generally is present in a mole-to-mole ratio of the alkylating agent to protic solvent to compound comprising Formula (I) of about 1:0.05:1 to about 5:100:1, preferably from about 1:0.2:1 to about 2:5:1.

The reaction mixture also optionally includes a metal halide represented by the formula $MX_n$. It is envisioned that the reaction mixture may not include any metal halide. However, running the reaction with an alkylating agent in the further presence of a metal halide can even further improve the reaction rate and yield. In one embodiment, M is selected from the group consisting of Li, Na, K, Cs, Mg, Ca, and Ba; X is selected from the group consisting of Cl, Br and I; and n=1 or 2.

The reaction mixture also includes a protic solvent. Suitable examples of protic solvents include water, alcohol, inorganic acid and organic acid. They include, but are not limited to water, methanol, ethanol, isopropanol, n-propanol, isobutanol, n-butanol, s-butanol, t-butanol, formic acid, acetic acid, propionic acid and combinations thereof. In an exemplary embodiment the protic solvent is water. The amount of protic solvent in the reaction mixture may vary but generally is present in a mole-to-mole ratio of the alkylating agent to protic solvent to amount of compound comprising Formula (I) of about 1:0.05:1 to about 5:100:1, preferably from about 1:0.2:1 to about 2:5:1.

The reaction mixture, as detailed herein, also optionally includes an aprotic solvent. While it is envisioned that the reaction mixture may not include any aprotic solvent, typically an aprotic solvent is included. Non-limiting examples of suitable aprotic solvents include ether solvents, acetone, acetonitrile, benzene, diethoxymethane, N,N-dimethylformamide (DMF), dimethyl sulfoxide (DMSO), N,N-dimethylpropionamide, 1,3-dimethyl-3,4,5,6-tetrahydro-2(1H)-pyrimidinone (DMPU), 1,3-dimethyl-2-imidazolidinone (DMI), 1,2-dimethoxyethane (DME), dimethoxymethane, bis(2-methoxyethyl)ether, N,N-dimethylacetamide (DMAC), N-methyl-2-pyrrolidinone (NMP), ethyl acetate, ethyl formate, ethyl methyl ketone, formamide, hexachloroacetone, hexamethylphosphoramide, methyl acetate, N-methylacetamide, N-methylformamide, methylene chloride, nitrobenzene, nitromethane, propionitrile, sulfolane, tetramethylurea, tetrahydrofuran (THF), 2-methyl tetrahydrofuran, toluene, trichloromethane, chloroform, dichloromethane, and combinations thereof. In an exemplary embodiment the reaction mixture will include NMP as the aprotic solvent. The amount of aprotic solvent in the reaction mixture, if present, may vary but generally is present in a weight-to-weight ratio with respect to the compound comprising Formula (I), of about 0.5:1 to about 10:1, in one embodiment is present in a weight-to-weight ratio of about 1:1 to about 10:1, and in another embodiment is present in a weight-to-weight ratio of about 0.05:1 to about 4:1.

The reaction mixture, as detailed herein, also optionally includes a proton acceptor to further favor the N-alkylation of secondary amines over N-alkylation of tertiary amines and O-alkylation of phenol at position C-3. As shown in the Examples, inclusion of a proton acceptor provides very high quantitative yields of the desired tertiary amine product. As such, the reaction mixture may comprise from about 0:1 to about 5:1, preferably from about 0.5:1 to about 4:1, in a mole-to-mole ratio of the proton acceptor to the compound comprising Formula I. While it is envisioned that the reaction mixture may not include any proton acceptor, typically a proton acceptor is included. Suitable proton acceptors include organic and inorganic bases, and combinations thereof. The proton acceptor typically has a pKa between about 6 and about 11, preferably between about 7 and about 9. Suitable proton acceptors having this characteristic include, but are not limited to, borate salts (such as, for example, $NaBO_3$), di- and tri-basic phosphate salts (such as, for example, $Na_2HPO_4$ and $Na_3PO_4$, and the like), bicarbonate salts (such as, for example, $NaHCO_3$, $KHCO_3$, $LiCO_3$, and the like), carbonate salts (such as, for example, $Na_2 CO_3$, $K_2CO_3$, $Li_2CO_3$, and the like), organic bases (such as, for example, pyridine, triethylamine, tripropylamine, tributylamine, diisopropylethylamine, N-methylmorpholine, N,N-dimethylaminopyridine), and mixtures of any of the above. In an exemplary embodiment, the reaction mixture will include triethylamine as a proton acceptor.

(b) Reaction Conditions

In general, the reaction may be conducted at a temperature that ranges from about 20° C. to about 120° C. for a period of time that is sufficient to convert a substantial portion of the compound comprising Formula (I) to the compound comprising Formula (II). In an exemplary embodiment, the temperature of the reaction may range from about 30° C. to about 85° C. In another exemplary embodiment, the temperature of the reaction may range from about 50° C. to about 100° C. In another exemplary embodiment, the temperature of the reaction may range from about 65° C. to about 85° C. The reaction is preferably performed under ambient pressure, and preferably in an inert atmosphere (e.g., nitrogen or argon).

Typically, the reaction is allowed to proceed for a sufficient period of time until the reaction is complete, as determined by chromatography (e.g., HPLC). In this context, a "completed reaction" generally means that the reaction mixture contains a significantly diminished amount of compounds comprising Formula (I) and a significantly increased amount of compounds comprising Formula (II) compared to the amounts of each present at the beginning of the reaction. Typically, the amount of compounds comprising Formula (I) remaining in the reaction mixture may be less than about 2%, and preferably less than about 1%.

When the reaction is completed, the reaction mixture is cooled to at least about room temperature (about 20° C.) and water is added to form a precipitate comprising the compound comprising Formula (II). The reaction may also optionally be cooled further to about 0° C. to about 5° C. For example, as detailed in Example 2, the reaction mixture is cooled from the reaction temperature (i.e., around 70° C. to about 85° C.) to about room temperature then to about 5° C. Upon precipitation of the compound comprising Formula (II), the reaction mixture comprises the solvent, and unreacted compounds of Formula (I). The precipitate comprising the compound comprising Formula (II) is separated from the remaining reaction mixture by filtration, washed and dried to produce the final product, namely a compound comprising Formula (II). Typically the solid filtrate is washed with water and then dried over a period of one or several hours in a vacuum chamber at an elevated temperature of about 65° C., or at a temperature of about 95° C. to about 105° C. without a vacuum.

The yield of the compound comprising Formula (II) may vary. Typically, the yield of the compound may range from about 90% to about 99%. In one embodiment, the yield of the compound is determined primarily by the amount of alkylated side products not comprising Formula (II) that are produced in proportion to the amount of compound comprising Formula (II). Specifically, such side products may comprise products resulting for example from the N-alkylation at position C-17 and O-alkylation at position C-3. For example, referring to Reaction Scheme 4, given a reaction mixture in which the compounds comprising Formula (Ib-1) and (IIb-2) are (+) enantiomers, the process may produce compounds comprising Formula (II-3) and compounds comprising Formula (IIb-4):

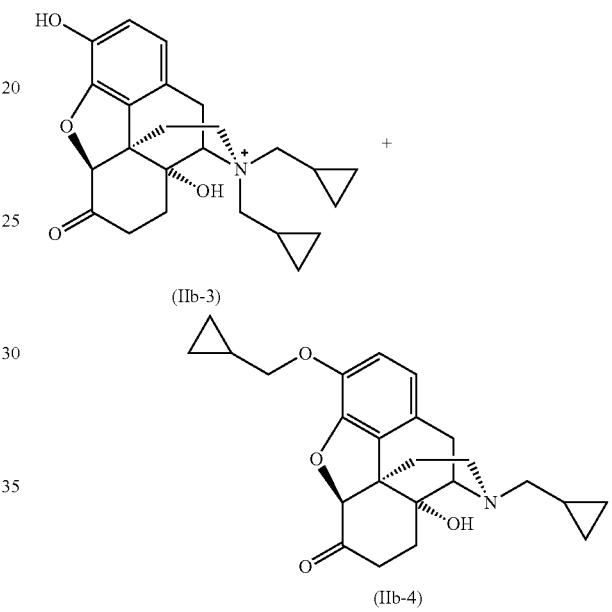

(IIb-3)

(IIb-4)

In an exemplary embodiment, the process results in the formation of compounds comprising Formula (IIb-3) and (IIb-4) that together comprise an amount less than 2% by weight, and preferably less than 1% by weight, of the total compounds formed by the reaction.

Similarly, the process minimizes the production of such side products when the (−) enantiomers are used. For example, referring again to Reaction Scheme 4, given a reaction mixture in which the compounds comprising Formula (Ib-1) and (IIb-2) are (−) enantiomers, the process may produce

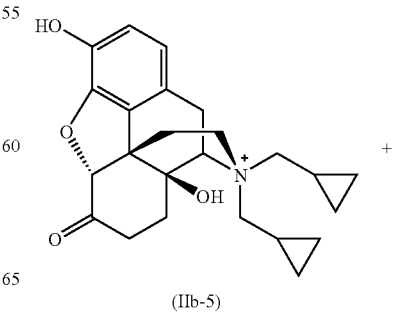

(IIb-5)

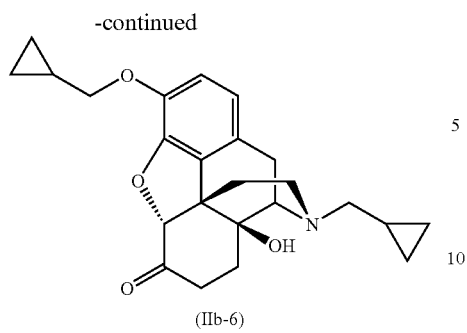

(IIb-6)

compounds comprising Formula (IIb-5) and compounds comprising Formula (IIb-6):

In an exemplary embodiment, the process results in the formation of compounds comprising Formula (IIb-5) and (IIb-6) that together comprise an amount less than 2% by weight, and preferably less than 1% by weight, of the total compounds formed by the reaction.

Similarly, referring for example for to Reaction Scheme 5, the process may result in the formation of compounds comprising tertiary amines at position C-17 and compounds that are alkylated at position C-3. In an exemplary embodiment, the process results in the formation of such side products in amounts that together comprise less than about 2% by weight, and preferably less than 1% by weight, of the total amount of products formed by the reaction.

(II) Stereochemistry and Enantiomers

Any of the compounds comprising any of Formulas (I) or (II) may have a (−) or (+) orientation with respect to the rotation of polarized light based on whether the starting material used is in the (−) or (+) opiate absolute form. More specifically, each chiral center may have an R or an S configuration. The compounds formed by the processes of the invention comprise morphinans. For purposes of illustration, the ring atoms of a morphinan compound are numbered as diagrammed below.

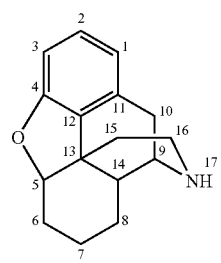

These morphinan compounds are recognized to have an alpha face and a beta face. Some compounds described herein, such as compounds comprising Formula (II), may have at least three chiral centers, namely carbons C9, C13, and C14, provided that the C15 and C16 atoms are both on the alpha face of the molecule or both on the beta face of the molecule. At each chiral center, the stereochemistry at the carbon atom is independently R or S.

Some compounds described herein, such as compounds comprising Formula (IIa), may have at least four chiral centers, namely carbons C5, C9, C13, and C14, provided that the C15 and C16 atoms are both on the alpha face of the molecule or both on the beta face of the molecule. At each chiral center, the stereochemistry at the carbon atom is independently R or S.

The invention also encompasses use of pharmaceutically acceptable salts of any of the compounds described herein. Exemplary salts include without limitation hydrochloride, hydrobromide, phosphate, sulfate, methansulfonate, acetate, formate, tartaric acid, maleic, malic, citrate, isocitrate, succinate, lactate, gluconate, glucuronate, pyruvate, oxalate, fumarate, propionate, aspartate, glutamate, benzoate, methyl fluoride, methyl chloride, methyl bromide, methyl iodide, and the like.

DEFINITIONS

The compounds described herein may have asymmetric centers. Compounds of the present invention containing an asymmetrically substituted atom may be isolated in optically active or racemic form. All chiral, diastereomeric, racemic forms and all geometric isomeric forms of a structure are intended, unless the specific stereochemistry or isomeric form is specifically indicated. All processes used to prepare compounds of the present invention and intermediates made therein are considered to be part of the present invention.

The term "acyl," as used herein alone or as part of another group, denotes the moiety formed by removal of the hydroxy group from the group COOH of an organic carboxylic acid, e.g., RC(O)—, wherein R is $R^1$, $R^1O$, $R^1R^2N$—, or $R^1S$—, $R^1$ is hydrocarbyl, heterosubstituted hydrocarbyl, or heterocyclo, and $R^2$ is hydrogen, hydrocarbyl or substituted hydrocarbyl.

The term "acyloxy," as used herein alone or as part of another group, denotes an acyl group as described above bonded through an oxygen linkage (O), e.g., RC(O)O— wherein R is as defined in connection with the term "acyl."

The term "alkyl" as used herein describes groups which are preferably lower alkyl containing from one to eight carbon atoms in the principal chain and up to 20 carbon atoms. They may be straight or branched chain or cyclic and include methyl, ethyl, propyl, isopropyl, butyl, hexyl and the like.

The term "alkenyl" as used herein describes groups which are preferably lower alkenyl containing from two to eight carbon atoms in the principal chain and up to 20 carbon atoms. They may be straight or branched chain or cyclic and include ethenyl, propenyl, isopropenyl, butenyl, isobutenyl, hexenyl, and the like.

The term "alkynyl" as used herein describes groups which are preferably lower alkynyl containing from two to eight carbon atoms in the principal chain and up to 20 carbon atoms. They may be straight or branched chain and include ethynyl, propynyl, butynyl, isobutynyl, hexynyl, and the like.

The term "aromatic" as used herein alone or as part of another group denotes optionally substituted homo- or heterocyclic aromatic groups. These aromatic groups are preferably monocyclic, bicyclic, or tricyclic groups containing from 6 to 14 atoms in the ring portion. The term "aromatic" encompasses the "aryl" and "heteroaryl" groups defined below.

The term "aryl" or "Ar" as used herein alone or as part of another group denote optionally substituted homocyclic aromatic groups, preferably monocyclic or bicyclic groups containing from 6 to 12 carbons in the ring portion, such as phenyl, biphenyl, naphthyl, substituted phenyl, substituted biphenyl or substituted naphthyl. Phenyl and substituted phenyl are the more preferred aryl.

The terms "halogen" or "halo" as used herein alone or as part of another group refer to chlorine, bromine, fluorine, and iodine.

The term "heteroatom" shall mean atoms other than carbon and hydrogen.

The terms "heterocyclo" or "heterocyclic" as used herein alone or as part of another group denote optionally substituted, fully saturated or unsaturated, monocyclic or bicyclic, aromatic or non-aromatic groups having at least one heteroatom in at least one ring, and preferably 5 or 6 atoms in each ring. The heterocyclo group preferably has 1 or 2 oxygen atoms and/or 1 to 4 nitrogen atoms in the ring, and is bonded to the remainder of the molecule through a carbon or heteroatom. Exemplary heterocyclo groups include heteroaromatics as described below. Exemplary substituents include one or more of the following groups: hydrocarbyl, substituted hydrocarbyl, hydroxy, protected hydroxy, acyl, acyloxy, alkoxy, alkenoxy, alkynoxy, aryloxy, halogen, amido, amino, cyano, ketals, acetals, esters and ethers.

The term "heteroaryl" as used herein alone or as part of another group denote optionally substituted aromatic groups having at least one heteroatom in at least one ring, and preferably 5 or 6 atoms in each ring. The heteroaryl group preferably has 1 or 2 oxygen atoms and/or 1 to 4 nitrogen atoms in the ring, and is bonded to the remainder of the molecule through a carbon. Exemplary heteroaryls include furyl, benzofuryl, oxazolyl, isoxazolyl, oxadiazolyl, benzoxazolyl, benzoxadiazolyl, pyrrolyl, pyrazolyl, imidazolyl, triazolyl, tetrazolyl, pyridyl, pyrimidyl, pyrazinyl, pyridazinyl, indolyl, isoindolyl, indolizinyl, benzimidazolyl, indazolyl, benzotriazolyl, tetrazolopyridazinyl, carbazolyl, purinyl, quinolinyl, isoquinolinyl, imidazopyridyl and the like. Exemplary substituents include one or more of the following groups: hydrocarbyl, substituted hydrocarbyl, hydroxy, protected hydroxy, acyl, acyloxy, alkoxy, alkenoxy, alkynoxy, aryloxy, halogen, amido, amino, cyano, ketals, acetals, esters and ethers.

The terms "hydrocarbon" and "hydrocarbyl" as used herein describe organic compounds or radicals consisting exclusively of the elements carbon and hydrogen. These moieties include alkyl, alkenyl, alkynyl, and aryl moieties. These moieties also include alkyl, alkenyl, alkynyl, and aryl moieties substituted with other aliphatic or cyclic hydrocarbon groups, such as alkaryl, alkenaryl and alkynaryl. Unless otherwise indicated, these moieties preferably comprise 1 to 20 carbon atoms.

The "substituted hydrocarbyl" moieties described herein are hydrocarbyl moieties which are substituted with at least one atom other than carbon, including moieties in which a carbon chain atom is substituted with a hetero atom such as nitrogen, oxygen, silicon, phosphorous, boron, sulfur, or a halogen atom. These substituents include halogen, heterocyclo, alkoxy, alkenoxy, aryloxy, hydroxy, protected hydroxy, acyl, acyloxy, nitro, amino, amido, nitro, cyano, ketals, acetals, esters and ethers.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

Having described the invention in detail, it will be apparent that modifications and variations are possible without departing from the scope of the invention defined in the appended claims.

EXAMPLES

The following examples illustrate various iterations of the invention.

Example 1

Synthesis of Naltrexone by Direct N-Alkylation of Noroxymorphone with an Alkyl Halide Naltrexone was prepared in high yield by direct N-alkylation of noroxymorphone with an alkyl halide in the presence of a protic solvent. Accordingly, 5.5 g of noroxymorphone, 16.5 mL of N-methyl-2-pyrrolidinone (NMP), and 1.65 mL of water were added to a flask (100 mL, 3 necked). The flask was flushed with nitrogen, and the reaction mixture was kept under nitrogen throughout the reaction. Next, 2.4 mL of bromomethylcyclopropane and 2.5 mL of triethylamine ($NEt_3$) were added to the flask, which was then heated at 70° C. for 2 h. An additional 2.5 mL of $NEt_3$ was added to the flask, and the mixture was heated at 70° C. for 7.5 h. HPLC analysis revealed that the reaction is completed with noroxymorphone at less than two percent or one percent and undesired side products such as quaternary ammonium salt and O-alkylation of phenol group were present at less than two percent or were undetectable. The mixture was cooled to room temperature, and water (82.5 g) was added to give a precipitate. The mixture was stirred for 1 h and then filtered. The solid was washed with water (2×5.5 mL) and dried under vacuum at 65° C. for 18 h to give 5.68 g of naltrexone as solid.

Example 2

Synthesis of (+)-Naltrexone

A similar method of synthesis was used to prepare (+)-naltrexone in high yield. For this, a flask (100 mL, 3 necked) was charged with 5.5 g of (+)-noroxymorphone, 16.5 mL of NMP, and 1.65 mL of water. The flask was flushed with nitrogen, and the reaction mixture was kept under nitrogen throughout the reaction. Next, 1.86 mL of bromomethylcyclopropane and 2.5 mL of $NEt_3$ were added to the flask, which was heated at 70° C. for 2.5 h. An additional 2.5 mL of $NEt_3$ was added to the flask, and the mixture was heated at 70° C. for 2.5 h. An additional 0.56 mL of bromomethylcyclopropane was added, and the mixture was heated at 70° C. for 2.5 h. HPLC analysis confirmed that the reaction is completed with noroxymorphone at less than two percent or one percent and the undesired side products were present at less than two percent or were undetectable. The mixture was cooled to room temperature, and water (82.5 g) was added to give a precipitate. The pH of the mixture was adjusted to pH 6 using 4 N HCl. The mixture was stirred for 30 min and then filtered to give 0.3 g solid. The pH of the filtrate was adjusted to pH 7-7.5 with c-$NH_4OH$ to give a precipitate and the mixture was stirred for 30 min. The pH of the filtrate was adjusted to pH 8.5-9.5 solid with c-$NH_4OH$ to give more precipitate. The mixture was cooled to 0° C. for 1 h, after which the mixture was filtered. The solid was washed with water (2×5.5 mL) and dried under vacuum at 65° C. for 18 h to give 5.38 g of (+)-naltrexone as solid.

Example 3

Synthesis of (+)-Naltrexone in the Presence of a Large Excess of Alkyl Halide

The following example was designed to determine the efficiency of this process when it is carried out in the presence of a large excess of alkyl halide. A mixture of (+)-noroxymorphone (5.00 g), acetonitrile (ACN) (20 mL), water (1.50 mL), NMP (15 mL), bromomethylcyclopropane (2.4 mL), and NEt$_3$ (2.4 mL) was heated at 70-85° C. for 28 h. HPLC analysis showed that both of undesired side products such as quaternary ammonium salt and O-alkylation of phenol group were less than two percent. Additional bromomethylcyclopropane (1.74 mL) was added and the reaction mixture was heated for another 6 h. HPLC analysis showed that both undesired side products quaternary ammonium salt and O-alkylation of phenol group were still less than two percent.

Example 4

Synthesis of (+)-N-cyclopropylmethyl-6,7-dihydro-northebaine

A mixture of (+)-6,7-dihydro-northebaine (5.00 g), NMP (10.0 mL), NaHCO$_3$ (5.00 g) and isopropanol (IPA; 2.50 mL) was stirred for 10 min. The reactor was flashed with nitrogen and the reaction maintained under nitrogen throughout. Cylopropylmethylbromide (2.20 mL) was added to the reaction mixture and the mixture was gradually heated to 68° C. over a period of 60 minutes and then maintained at 68° C. for another 120 minutes. HPLC analysis confirmed that the undesired side products were present at less than one percent and that the starting material was less than 1% weight/weight. Water was added (15 mL), then c-NH$_4$OH added (2 mL), and the resulting mixture stirred for 30 minutes and cooled to 35° C. Water was again added (15 mL), and more c-NH$_4$OH added (3 mL). The mixture was stirred at 20° C. for a period of 1 h and then filtered and washed with water (6×5 mL). The resulting solid was oven dried under vacuum at 65° C. for 18 hours to give 5.58 g of (+)-N-cyclopropylmethyl-6,7-dihydro-northebaine as a white solid (95% isolated yield).

Example 5

Synthesis of (−)-Naltrexone—Trial 1

A mixture of 11.0 g (−)-noroxymorphone, 3.8 mL bromomethylcyclopropane, 33 mL of NMP, 3.3 mL water, and 5 mL NEt$_3$ was heated at 70° C. for 2 h. Then another 5 mL NEt$_3$ was added, and 0.5 h later 1.2 ml of bromomethylcyclopropane was added. Heating was continued for 2 h. The mixture was cooled to room temperature and 165 ml water was dripped in. Because the pH was over 9.5 (pH paper), it was not adjusted. Filtration, washing with water, and drying in vacuo yielded 11.65 g (89% yield) of (−)-naltrexone. HPLC analysis revealed naltrexone (96.65 area %) and 3-cyclopropylmethyl naltrexone (0.85 area %).

Example 6

Synthesis of (−)-Naltrexone—Trial 2

A mixture of 8.20 g (−)-noroxymorphone, 5.0 g of bromomethylcyclopropane, 45 mL of NMP, and 5.3 g of sodium bicarbonate was heated for 6 h at 70-80° C. A mixture of 15 g of NaCl in 150 mL of water was heated to 50° C. in a separate flask. The reaction mixture was dripped into the NaCl solution over a period of 50 minutes. The reaction mixture was cooled to room temperature, filtered, and dried to give 7.15 g of (−)-naltrexone. HPLC analysis revealed naltrexone (88.44 area %) and 3-cyclopropylmethyl naltrexone (10.64 area %).

Example 7

Synthesis of (−)-Naltrexone—Trial 3

A mixture of 8.29 g (−)-noroxymorphone, 5.0 g of bromomethylcyclopropane, 45 mL of NMP, 4.5 mL water, and 5.3 g of sodium bicarbonate was heated for 4 h at 80° C. A mixture of 15 g of NaCl in 150 mL of water was heated to 50° C. in a separate flask. The reaction mixture was dripped into the NaCl solution over 20 minutes. Concentrated ammonium hydroxide, 3 mL, was added to give a pH over 9. Cooling, filtration, washing with water, and drying gave 9.1 g of (−)-naltrexone. HPLC analysis revealed naltrexone (91.94 area %) and 3-cyclopropylmethyl naltrexone (1.08 area %).

Example 8

Synthesis of (−)-Naltrexone—Trial 4

A mixture of 8.24 g (−)-noroxymorphone, 5.1 g of bromomethylcyclopropane, 45 mL of NMP, 8.0 mL water, and 5.3 g of sodium bicarbonate was heated for 4 h at 80° C. A mixture of 15 g of NaCl in 150 mL of water was heated to 50° C. in a separate flask. The reaction mixture was dripped into the NaCl solution over 20 minutes. Concentrated ammonium hydroxide, 3 mL, was added to give a pH over 9. Cooling, filtration, washing with water, and drying gave 7.89 g of (−)-naltrexone. HPLC analysis revealed naltrexone (97.41 area %) and 3-cyclopropylmethyl naltrexone (0.97 area %).

Example 9

Synthesis of (−)-Naltrexone—Trial 5

A mixture of 8.23 g (−)-noroxymorphone, 5.2 g of bromomethylcyclopropane, 45 mL of NMP, 4.5 mL ethanol, and 5.3 g of sodium bicarbonate was heated for 3.5 h at 80° C. A mixture of 15 g of NaCl in 150 mL of water was heated to 50° C. in a separate flask. The reaction mixture was dripped into the NaCl solution over 20 minutes. Concentrated ammonium hydroxide, 3 mL, was added to give a pH over 9. Cooling, filtration, washing with water, and drying gave 7.47 g of (−)-naltrexone. HPLC analysis revealed naltrexone (93.86 area %) and 3-cyclopropylmethyl naltrexone (4.83 area %).

Example 10

Synthesis of (−)-Naltrexone—Trial 6

A mixture of 8.22 g (−)-noroxymorphone, 5.2 g of bromomethylcyclopropane, 45 mL of dimethylformamide (DMF), 4.5 mL water, and 5.3 g of sodium bicarbonate was heated for 3 h at 80° C. A mixture of 15 g of NaCl in 150 mL of water was heated to 50° C. in a separate flask. The reaction mixture was dripped into the NaCl solution over 20 minutes. Concentrated ammonium hydroxide, 3 mL, was added to give a pH over 9. Cooling, filtration, washing with water, and drying gave 8.44 g of (−)-naltrexone. HPLC analysis revealed naltrexone (98.45 area %) and 3-cyclopropylmethyl naltrexone (0.57 area %).

Example 11

Synthesis of (−)-Naltrexone—Trial 7

A mixture of 8.26 g (−)-noroxymorphone, 5.2 g of bromomethylcyclopropane, 45 mL of DMF, 4.5 mL ethanol, and 5.5 g of sodium bicarbonate was heated for 3 h at 80° C. A mixture of 15 g of NaCl in 150 mL of water was heated to 50° C. in a separate flask. The reaction mixture was dripped into the NaCl solution over 20 minutes. Concentrated ammonium hydroxide, 3 mL, was added to give a pH over 9. Cooling, filtration, washing with water, and drying gave 7.50 g of (−)-naltrexone. HPLC analysis revealed naltrexone (98.06 area %) and 3-cyclopropylmethyl naltrexone (0.70 area %).

Example 12

Synthesis of (−)-Naltrexone—Trial 8

A mixture of 8.26 g (−)-noroxymorphone, 5.2 g of bromomethylcyclopropane, 45 mL of N,N-dimethylacetamide, 4.5 mL water, and 5.3 g of sodium bicarbonate was heated for 4.5 h at 80° C. A mixture of 15 g of NaCl in 150 mL of water was heated to 50° C. in a separate flask. The reaction mixture was dripped into the NaCl solution over 20 minutes. Concentrated ammonium hydroxide, 3 mL, was added to give a pH over 9. Cooling, filtration, washing with water, and drying gave 9.10 g of (−)-naltrexone. HPLC analysis revealed naltrexone (98.82 area %) and 3-cyclopropylmethyl naltrexone (0.88 area %)

What is claimed is:

1. A process for the preparation of a compound comprising Formula (II) from a compound comprising Formula (I) according to the following reaction:

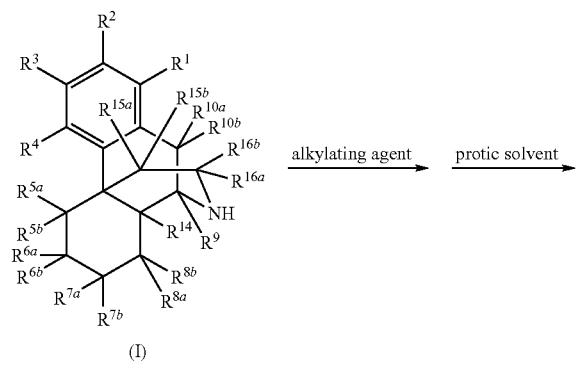

(I)

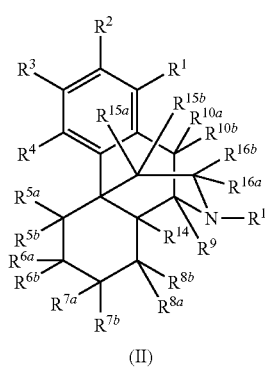

(II)

wherein:
the alkylating agent is selected from the group consisting of alkyl halide represented by the formula $R^{17}X$, and dialkyl sulfate represented by the formula $R^{17}_2SO_4$, wherein $R^{17}$ is selected from the group consisting of hydrocarbyl and substituted hydrocarbyl, and X is selected from the group consisting of Cl, Br and I;

$R^1$, $R^2$, $R^3$, and $R^4$ are independently selected from the group consisting of hydrogen, halogen, hydroxyl, SH, —$SR^{1611}$, —$OR^{1611}$, and —$NR^{1611}R^{1612}$; hydrocarbyl, and substituted hydrocarbyl;

$R^{5a}$, $R^{5b}$, $R^{6a}$, $R^{6b}$, $R^{7a}$, $R^{7b}$, $R^{8a}$ $R^{8b}$, $R^9$, $R^{10a}$ $R^{10b}$, $R^{15a}$ $R^{15b}$, $R^{16a}$ $R^{16b}$, and $R^{14}$ are independently selected from the group consisting of hydrogen, halogen, hydroxyl, SH, —$SR^{1611}$, —$OR^{1611}$, and —$NR^{1611}R^{1613}$; hydrocarbyl, and substituted hydrocarbyl, wherein any pair of $R^{\#a}$ and $R^{\#b}$ wherein # is any one of 5, 6, 7, 8, 9, 10, 15, 16, optionally together form a group selected from the group consisting of =O, =S, and =$NR^{1613}$;

$R^{1611}$, $R^{1612}$ and $R^{1613}$ are independently selected from the group consisting of hydrocarbyl, and substituted hydrocarbyl;

provided that one or more of $R^1$, $R^2$, $R^3$, $R^4$, $R^{5a}$, $R^{5b}$, $R^{6a}$, $R^{6b}$, $R^{7a}$, $R^{7b}$, $R^{8a}$ $R^{8b}$, $R^{9a}$, $R^{10a}$ $R^{10b}$, $R^{15a}$ $R^{15b}$, $R^{16a}$ $R^{16b}$, and $R^{14}$ may come together to form one or more carbocyclic or heterocyclic rings.

2. The process of claim 1, wherein the alkylating agent is selected from the group consisting of an alkyl halide having from one to ten carbon atoms, and a substituted alkyl halide having from one to ten carbon atoms; and the protic solvent is selected from the group consisting of water, alcohol, inorganic acid and organic acid.

3. The process of claim 1, further comprising conducting the reaction in the presence of an agent selected from the group consisting of a proton acceptor; an aprotic solvent; a metal halide represented by the formula $MX_n$, wherein M is selected from the group consisting of Li, Na, K, Cs, Mg, Ca, and Ba, X is selected from the group consisting of Cl, Br and I, and n=1 or 2; and combinations thereof.

4. The process of claim 1, wherein the mole-to-mole ratio of the alkylating agent to protic solvent to compound comprising Formula (I) is from about 1:0.2:1 to about 2:5:1; the reaction is conducted in the presence of a proton acceptor; and the reaction is conducted at a temperature ranging from about 30° C. to about 85° C.

5. The process of claim 1, wherein the compounds comprising Formula (I) and (II) are (+) enantiomers, (−) enantiomers, and combinations of both; and the configuration of C-9, C-13, and C-14, respectively, in the compounds comprising Formula (I) and (II) is selected from the group consisting of RRR, RRS, RSR, RSS, SRR, SRS, SSR, and SSS, provided, however, that the C-15 and C-16 atoms are either both on the alpha face of the compound or the beta face of the compound.

6. The process of claim 1, wherein the formation of compounds comprising tertiary amines at position C-17 and compounds alkylated at $R^3$ when it comprises oxygen together comprise less than 2% by weight of the total compounds formed by the reaction.

7. The process of claim 1, wherein the yield of the compound comprising Formula (II) is greater than 90%.

8. A process for the preparation of a compound comprising Formula (IIa) from a compound comprising Formula (Ia) according to the following reaction:

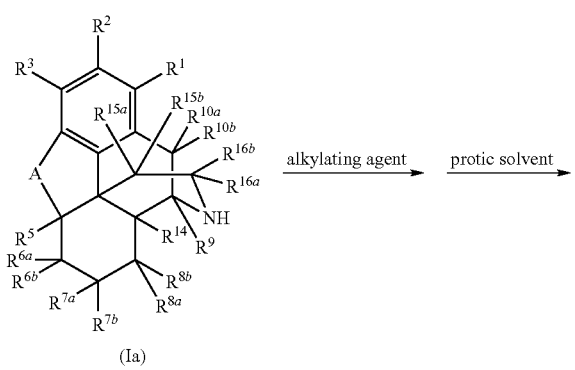

(Ia)

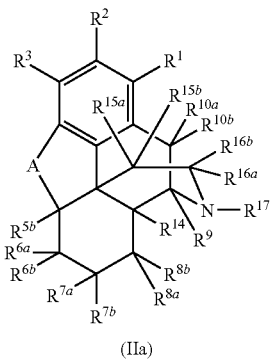

(IIa)

wherein:
the alkylating agent is selected from the group consisting of alkyl halide represented by the formula $R^{17}X$, and dialkyl sulfate represented by the formula $R^{17}_2SO_4$, wherein $R^{17}$ is selected from the group consisting of hydrocarbyl and substituted hydrocarbyl, and X is selected from the group consisting of Cl, Br and I;

A is a heteroatom selected from oxygen and sulfur;

$R^1$, $R^2$, $R^3$, and $R^4$ are independently selected from the group consisting of hydrogen, halogen, hydroxyl, SH, —$SR^{1611}$, —$OR^{1611}$, and —$NR^{1611}R^{1612}$; hydrocarbyl, and substituted hydrocarbyl;

$R^5$, $R^{6a}$, $R^{6b}$, $R^{7a}$, $R^{7b}$, $R^{8a}R^{8b}$, $R^9$, $R^{10a}R^{10b}$, $R^{15a}R^{15b}$, $R^{16a}R^{16b}$, and $R^{14}$ are independently selected from the group consisting of hydrogen, halogen, hydroxyl, SH, —$SR^{1611}$, —$OR^{1611}$, and —$NR^{1611}R^{1613}$; hydrocarbyl, and substituted hydrocarbyl, wherein any pair of $R^{\#a}$ and $R^{\#b}$ wherein # is any one of 6, 7, 8, 9, 10, 15, 16, optionally together form a group selected from the group consisting of =O, =S, and =$NR^{1613}$;

$R^{1611}$, $R^{1612}$ and $R^{1613}$ are independently selected from the group consisting of hydrocarbyl, and substituted hydrocarbyl;

provided that one or more of $R^1$, $R^2$, $R^3$, $R^4$, $R^5$, $R^{6a}$, $R^{6b}$, $R^{7a}$, $R^{7b}$, $R^{8a}R^{8b}$, $R^{9a}$, $R^{10a}R^{10b}$, $R^{15a}R^{15b}$, $R^{16a}R^{16b}$, and $R^{14}$ may come together to form one or more carbocyclic or heterocyclic rings.

9. The process of claim 8, wherein the alkylating agent is selected from the group consisting an alkyl halide having from one to ten carbon atoms, and a substituted alkyl halide having from one to ten carbon atoms; and the protic solvent is selected from the group consisting of water, alcohol, inorganic acid and organic acid.

10. The process of claim 8, further comprising conducting the reaction in the presence of an agent selected from the group consisting of a proton acceptor; an aprotic solvent; a metal halide represented by the formula $MX_n$, wherein M is selected from the group consisting of Li, Na, K, Cs, Mg, Ca, and Ba, X is selected from the group consisting of Cl, Br and I, and n=1 or 2; and combinations thereof.

11. The process of claim 8, wherein the mole-to-mole ratio of the alkylating agent to protic solvent to compound comprising Formula (Ia) is from about 1:0.2:1 to about 2:5:1; the reaction is conducted in the presence of a proton acceptor; and the reaction is conducted at a temperature ranging from about 30° C. to about 85° C.

12. The process of claim 8, wherein the compounds comprising Formula (Ia) and (IIa) are (+) enantiomers; (−) enantiomers; and combinations of both; and the configuration of C-5, C-9, C-13, and C-14, respectively, in the compounds comprising Formula (Ia) and (IIa) is selected from the group consisting of RRRR, RRSR, RRRS, RRSS, RSRR, RSSR, RSRS, RSSS, SRRR, SRSR, SRRS, SRSS, SSRR, SSSR, SSRS, and SSSS, provided, however, that the C-15 and C-16 atoms are either both on the alpha face of the compound or the beta face of the compound.

13. The process of claim 8, wherein the formation of compounds comprising tertiary amines at position C-17 and compounds alkylated at $R^3$ when it comprises oxygen together comprise less than 2% by weight of the total compounds formed by the reaction.

14. The process of claim 8, wherein the yield of the compound comprising Formula (IIa) is greater than 90%.

15. The process of claim 8, wherein the process comprises the preparation of a compound comprising Formula (IIa-2) from a compound comprising Formula (Ia-1) according to the following reaction:

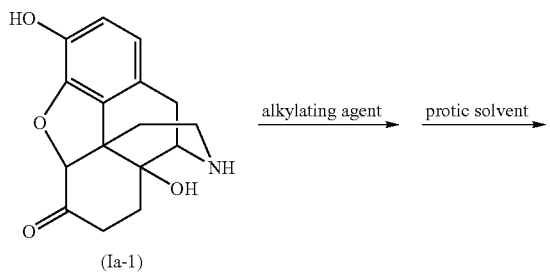

(Ia-1)

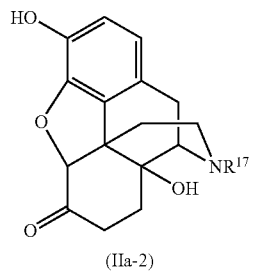

(IIa-2)

wherein the alkylating agent is selected from the group consisting an alkyl halide having from one to ten carbon atoms, and a substituted alkyl halide having from one to ten carbon atoms; and the protic solvent is selected from the group consisting of water, alcohol, inorganic acid and organic acid.

16. The process of claim 8, wherein the process comprises the preparation of a compound comprising Formula (IIb-2) from a compound comprising Formula (Ib-1) according to the following reaction:

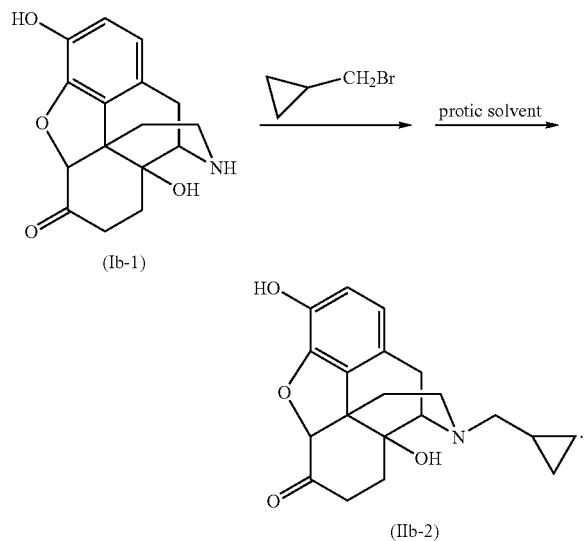

17. The process of claim 16, wherein the compounds comprising Formula (Ib-1) and (IIb-2) are (+) enantiomers; and the formation of compounds comprising Formula (IIb-3) and (IIb-4) together comprise less than 2% by weight of the total compounds formed by the reaction:

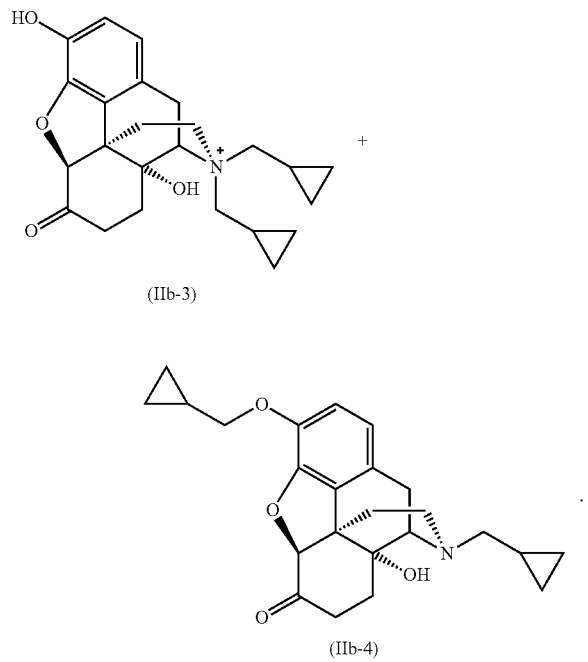

18. The process of claim 16, wherein the compounds comprising Formula (Ib-1) and (IIb-2) are (−) enantiomers; and the formation of compounds comprising Formula (IIb-5) and (IIb-6) together comprise less than 2% by weight of the total compounds formed by the reaction:

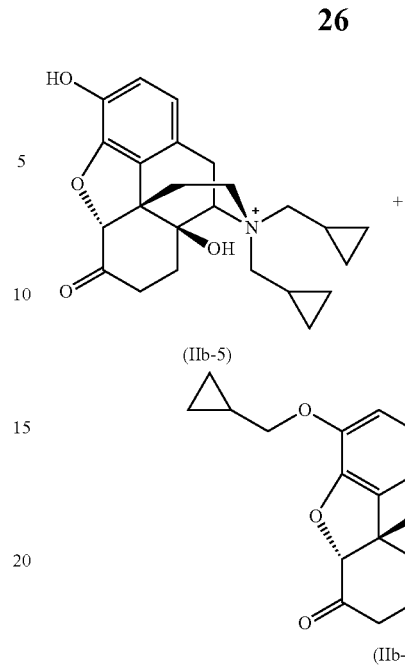

19. The process of claim 8, wherein the process comprises the preparation of a compound comprising Formula (IIc-2) from a compound comprising Formula (Ic-1) according to the following reaction:

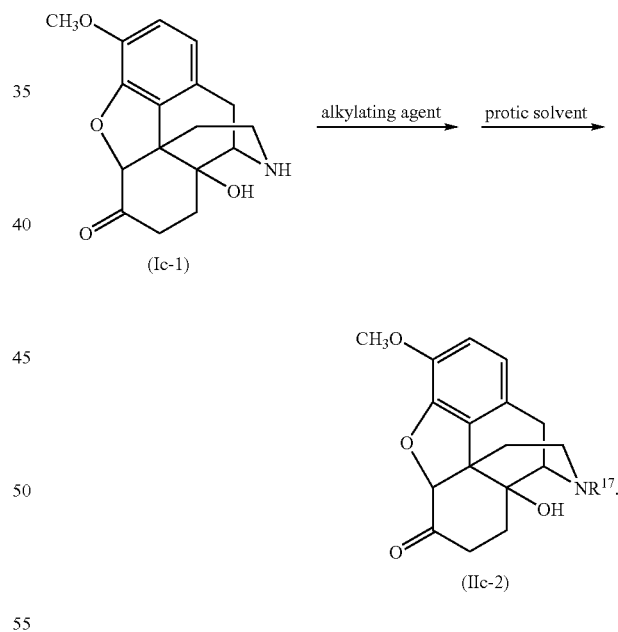

wherein the alkylating agent is selected from the group consisting an alkyl halide having from one to ten carbon atoms, and a substituted alkyl halide having from one to ten carbon atoms; and the protic solvent is selected from the group consisting of water, alcohol, inorganic acid and organic acid.

20. The process of claim 19, wherein the formation of compounds comprising tertiary amines at position C-17 and compounds that are alkylated at position C-3 together comprise less than 2% by weight of the total compounds formed by the reaction.

21. The process of claim 8, wherein the process comprises the preparation of a compound comprising Formula (IId-2) from a compound comprising Formula (Id-1) according to the following reaction:

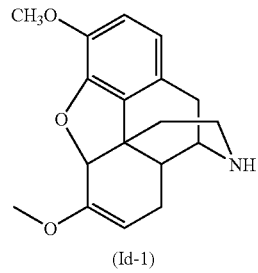 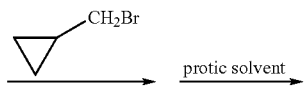 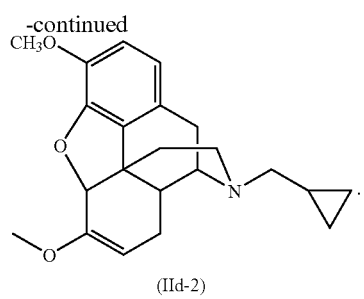

(Id-1) → (IId-2)

22. The process of claim 21, wherein the formation of compounds comprising tertiary amines at position C-17 and compounds that are alkylated at position C-3 together comprise less than 2% by weight of the total compounds formed by the reaction.

* * * * *